United States Patent [19]

Vella-Coleiro et al.

[11] 4,342,962
[45] Aug. 3, 1982

[54] METHOD FOR MEASURING COERCIVITY IN MAGNETIC MATERIALS

[75] Inventors: George P. Vella-Coleiro, Summit; Raymond Wolfe, New Providence, both of N.J.

[73] Assignee: Bell Telephone Laboratories, Incorporated, Murray Hill, N.J.

[21] Appl. No.: 142,013

[22] Filed: Apr. 21, 1980

[51] Int. Cl.³ .................... G01N 27/72; G01R 33/12
[52] U.S. Cl. .................................... 324/232; 324/210
[58] Field of Search ................ 324/210, 211, 212, 232

[56]  References Cited
PUBLICATIONS

Shumate, Jr., "Magnetooptic–Measurement Techniques . . ." IEEE Transactions on Magnetics, Sep. 1971, pp. 586–590.
Vella-Coleiro et al, "New Method for Routine Measurement . . ." IEEE Transactions on Magnetics, Sep. 1980, pp. 625–627.

Primary Examiner—Gerard R. Strecker
Assistant Examiner—Walter E. Snow
Attorney, Agent, or Firm—Bruce S. Schneider

[57] ABSTRACT

The coercivity of materials that are capable of supporting single wall magnetic domains are measured by an expedient and accurate technique. This technique requires that the material be placed in a static magnetic field having a gradual spatial gradient. Finger shaped domains produced in the material are then modulated by introduction of an AC magnetic field. Coercivity is obtained by measuring the distance the finger domains move due to the AC field.

10 Claims, 7 Drawing Figures

METHOD FOR MEASURING COERCIVITY IN MAGNETIC MATERIALS

BACKGROUND OF THE INVENTION

1. Field of the Invention

This invention relates to the measurement of magnetic properties and, in particular, to the measurement of magnetic properties of materials used in devices relying on movement of single wall magnetic domains.

2. Art Background

The performance of a device based on the movement of single wall magnetic domains through a material capable of supporting such domains, e.g., one with a garnet crystal structure, depends, to a significant extent, on the properties of the material. Among these properties is the coercivity of a single wall magnetic domain in the magnetic material, i.e., the difficulty of initiating the movement of the domain in the material. To insure the manufacture of devices having suitable properties and to insure the consistent functioning of circuits incorporating these devices, it is desirable to measure the coercivity of the domain supporting material during the manufacture process to determine whether it is sufficiently low to prevent unacceptable degradation of the properties of the finished device.

A variety of methods has been developed for measuring the coercivity of a domain supporting material, e.g., a garnet layer, utilized in a device. The most common method for measuring coercivity involves the measurement of the response to a stripe domain pattern to an oscillating magnetic field. In this approach, a random demagnetized stripe domain pattern, such as shown in FIG. 1, is employed. This domain pattern is subjected to an oscillating magnetic field and the extent of the modulation of the stripe width for a given field is measured. The data obtained are then plotted and the value of the field obtained by extrapolation to zero modulation of the domain width is defined as the coercivity of the magnetic garnet layer. (See R. D. Pierce, *Journal of Crystal Growth*, 27,299 (1974).) An alternative technique for measuring coercivity involves the monitoring of bubble translation in a pulsed field gradient. In this technique, single wall magnetic domains, i.e., bubbles, are produced in the domain supporting material. A pulsed field gradient is then repetitively applied to the material and its magnitude is increased until a bubble begins to move. The field at which translation initiates is considered the coercivity. (See Vella-Coleiro and Tabor, *Applied Physics Letters*, 27, 7 (1972).)

Each of the previously mentioned techniques has certain advantages and certain shortcomings. The oscillating stripe domain technique is an expedient method of measuring coercivity. However, this technique suffers from a large experimental error—generally greater than 50 percent. On the other hand, the bubble translation technique is an accurate method of measuring coercivity. However, this method is extremely tedious.

Neither of the previously mentioned techniques used for measuring coercivity is adaptable for quality control measurements. The oscillating stripe domain procedure is relatively fast and, therefore, is usable to measure the coercivity of a reasonable sampling of materials as they are used to make devices in a manufacturing facility. However, the inaccuracies inherent in this technique make it impossible to insure that the desired coercivities are being obtained. On the other hand, the bubble translation technique is too slow to be satisfactory for quality control measurements. Thus, as yet a coercivity measuring technique suitable for testing the reproducibility of coercivity in a production environment, is not available.

SUMMARY OF THE INVENTION

A rapid and reliable method for measuring the coercivity of material capable of supporting single wall magnetic domains is possible if an appropriate choice of magnetic field profile and of domain configuration is utilized in the measurement. This measuring method involves the use of finger domains (such as shown in FIG. 2) as the domain configuration that is utilized in the measurement. In a preferred embodiment, a static magnetic field having a relatively small spatial gradient is introduced. The domain supporting material is subjected to an AC magnetic field while being influenced by this static gradient field. The amplitude of the domain movement is recorded versus the amplitude of the AC field. (A plot such as shown in FIG. 3 is obtained.) A value for coercivity is determined from this plot.

Coercivity values are obtained in an expedient manner. The results achieved with the subject method are quite reproducible and are advantageously used for measuring coercivity.

DETAILED DESCRIPTION

Figure 1:
FIG. 1 represents a random magnetic stripe domain pattern used in some coercivity measurements.
Figure 2:
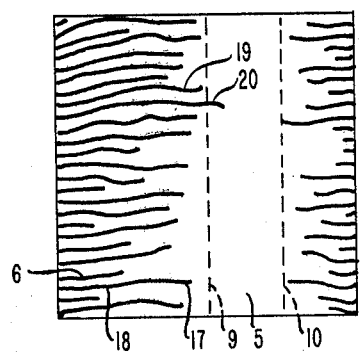
FIGS. 2 and 4 are domain patterns involved in the subject invention.

Measurements are performed on a material capable of supporting single wall magnetic domains, e.g., garnet materials, in which substantially parallel finger domains have been formed. An exemplary finger domain pattern in shown in FIG. 2. (The light and dark portions of the pattern are those produced due to the Faraday effect when polarized light passes through the domain supporting material and then is observed through an analyzer. The analyzer is arranged to selectively block light whose plane of polarization is rotated by domains of one polarity but not to block the light rotated in the opposite direction by domains of the other polarity. See T. H. O'Dell, "Magnetic Bubbles" John Wiley & Sons, New York, 1974, page 4, for description of the Faraday effect as it relates to garnet material.) A finger domain, for purposes of this invention, is defined by considering the configurations of the domains of each magnetic polarity in the region of the garnet where the measurement is to be made. First, it is determined which polarity type domain occupies the lesser area in the measurement region, i.e., which domain type is the minority type domain. A minority domain and only a minority domain is a finger domain when (1) it terminates within the region of the domain supporting material to be measured, (2) it is parallel or within 10 degrees of being parallel to the minority domain nearest to it (the direction of a domain is defined by a straight line that is the least-squares-fit to a boundary of the domain), and (3) beyond an imaginary line passing through its termination point and perpendicular to its direction, there are no other minority domains that both have a terminus within, and extend beyond, a 10 μm separation distance of its termination point. Preferably, this separation distance should be 20 μm and most advantageously 100 μm. The contrast between a finger pattern and stripe pattern can be seen by comparing FIG. 2 to FIG. 1. The black region, 18, in FIG. 2 terminates at 17, and is within 10 degrees of being parallel with its nearest neighbor, 6, thus satisfying criteria 1 and 2. Also, assuming imaginary lines 9 and 10 are 10 μm apart, criterion 3 is also satisfied. It should be noted that the domain 20 terminates beyond line 9 and within 10 μm of the end point of domain 19. However, domain 20 does not extend beyond the 10 μm distance, but instead extends back behind line 9. In contrast, the black regions in FIG. 1 obviously do not satisfy these criteria. For an acceptable measurement not all the minority domains need be finger domains. Generally, however, no less than 70 percent of the minority domain area in the region in which the measurement is performed should be of the finger type.

Figure 4:
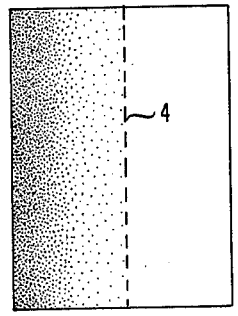

Finger domains are advantageously established by first producing a sea of single wall magnetic domains such as shown in FIG. 4. This is preferably done by temporarily subjecting the domain supporting material to a field whose direction and magnitude are sufficient to force the magnetic moment of the domain supporting material essentially into the plane of its surface. In garnet materials, this is done by utilizing an in-plane field greater than the anisotropy field of the material. For example, the material is encircled by a rectangular coil which is pulsed with a single half-cycle from a standard 115 V AC power line. In this manner, a field well in excess of 5 K Oe is easily produced. (It is desirable to maintain the field produced by the coil so that it is not exactly parallel to the plane of the material. This insures that substantially all of the bubbles in the sea of bubbles have the same polarity.) The area of the domain supporting material to be measured is subjected to a static gradient field where the amplitude of this field exceeds the saturation field of the domain supporting material somewhere in the measurement region of the material, but not throughout this region. (The gradient field, described below, used to make the actual measurement is also employable for this purpose.) With the static gradient field present, an oscillatory field with an amplitude of between 10 and 40 Oe and a frequency in the range of 2 Hz to 3 KHz is then utilized to convert the sea of bubbles into a finger domain pattern. (The domains after they are formed are preferably maintained by keeping them in the static field gradient.)

The measurement is performed while the finger domains are subjected to a static magnetic field having a weak spatial gradient across the portion of the garnet where the finger domains are to be measured. This static field should not have a substantial in-plane component in the measurement area, i.e., the component of magnetic field in the direction of the major surface of the domain supporting material should not be greater than 20 percent of the field required to force the magnetic moment of the domain supporting material into the plane of the material. Additionally, the mean field gradient of this static field within the measurement region, i.e., the mean of the derivative of the field magnitude with respect to each position on the domain supporting material, should be less than 10 Oe/μm, preferably less than 1 Oe/μm, to achieve the accuracy necessary for reliable measurement of coercivity. For materials that are capable of supporting large diameter bubbles, i.e., bubbles greater than 2 μm, and that have low coercivities less than 1 Oe, it is possible that gradients as large as 10 Oe/μm may produce data which when plotted do not show a sufficiently pronounced change in slope as compared to one such as seen at 22 in FIG. 3. This problem is easily corrected by reducing the magnitude of the field gradient. The static field should also be capable of maintaining the necessary finger domains. This is done in a preferred embodiment, by using a field such as 15 in FIG. 7 where the field value exceeds the saturation field of domain material within the measurement area and after exceeding this value does not go below it for a distance of at least 10 μm, preferably for at least 20 μm and most advantageously for at least 100 μm.

Figure 5:
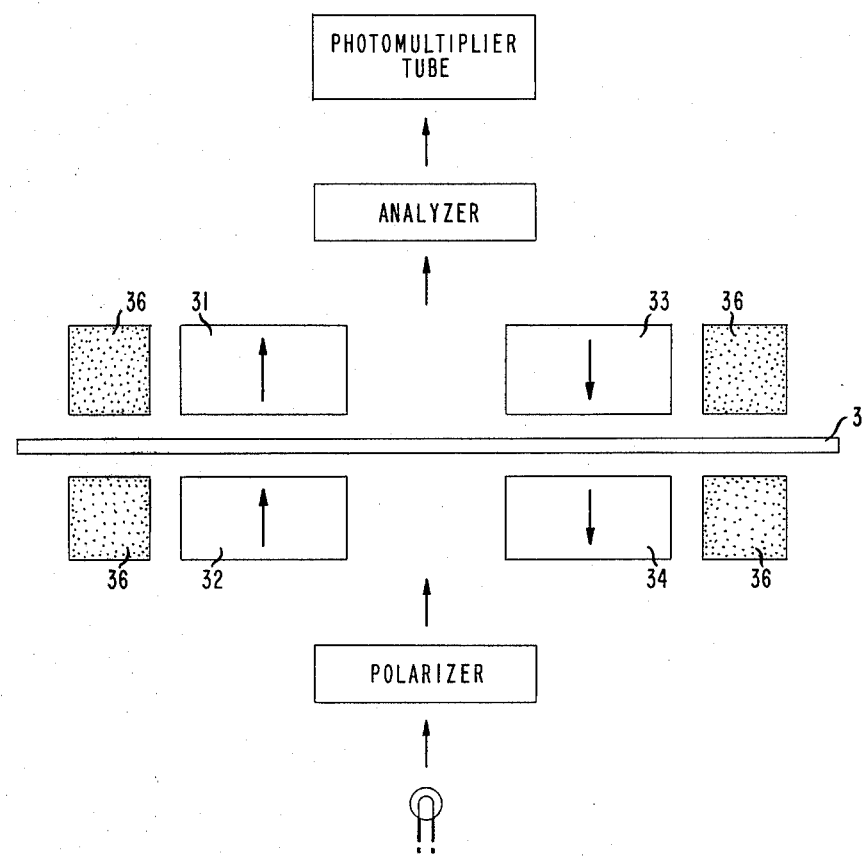
FIGS. 5, 6, and 7 illustrate configurations of magnetic fields used in conjunction with the subject invention.

The necessary weak gradient field is expediently produced by using permanent magnets. In a preferred embodiment, to insure that an excessively large in-plane field is not produced over the measurement area, a symmetrical magnet configuration is utilized. For example, the configuration of magnets 31, 32, 33, and 34 with poles as shown in FIG. 5 is employed. (The type of permanent magnet is not critical. Magnets composed of Sm-Co are suitable.) In this symmetric configuration, the in-plane lines of magnetic force for the magnets below and above the garnet film cancel and essentially no in-plane field is produced at the mid-plane. Displacement of the layer in the upward or downward direction from the mid-plane prevents total cancellation of the fields and, therefore, allows some in-plane component to form. However, if the surface of the domain supporting material is approximately midway between the upper and lower magnets, no substantial in-plane field is encountered.

Figure 6:
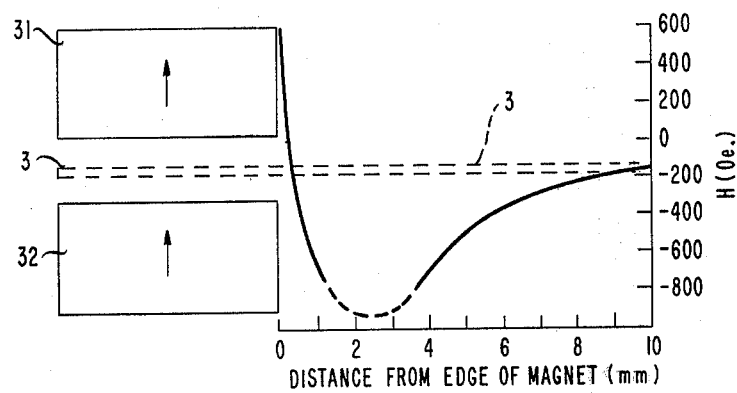
Figure 7:
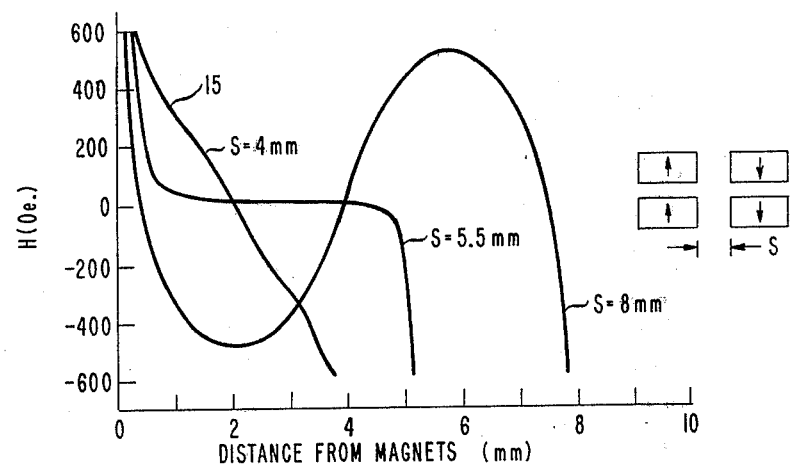

The permanent magnets used in the measurement produce a field whose magnitude at some point in the measurement region magnetically saturates the domain supporting material. This manifests itself in a region through the measurement area, e.g., the area between the dotted lines in FIG. 2, where only one domain polarity is present. Then the field gradient produced by these magnets is adjusted to the desired value by appropriately spacing the magnets. To determine if a magnet configuration and spacing is appropriate, the field produced by the magnets is measured by utilizing a series of samples having known single wall domain collapse field. A sea of single wall domains is produced in the samples as previously described. The samples are then placed between half of the entire set of magnets. To determine which magnets are to be employed in this half for the field measurement, an imaginary plane is drawn normal to the surface of the domain supporting material at the point where the saturation occurs and the magnets on one side of this plane are removed. The position on the magnetic film where the bubble domains terminate, e.g., the dotted line denoted 4 in FIG. 4, indicates the position where the field strength is equal to the collapse field. Thus, by using a series of materials, such as garnet materials, each having a known collapse field, the field at different positions due to half the complete set of permanent magnets is determined. The results of one such determination is shown in FIG. 6. (The dotted line 3 indicates the plane of the measured material; magnets 31 and 32 correspond to identically denoted magnets in FIG. 5.) A similar measurement and graph by the same technique is made for the set of magnets initially removed. By adding these two graphs, the overall field due to the entire set of magnets is determined. Each graph shows the field produced by a set of magnets as a function of the distance from a point fixed on one of the magnets in the set. To determine the field for all the magnets where the spacing between the point fixed on one set of magnets and that fixed on the other set is a given distance, x, the graphs are superimposed and added with the origin of one graph displaced a distance, x, from the origin of the other. As the relative positions of the magnets and thus the relative positions of the graphs change, it is possible that the field gradient also changes quite dramatically. For example, when the magnets are in the configuration as shown in FIG. 5, the overall field for a variety of separations, S, shown in FIG. 7, is obtained. By this procedure, a suitable spacing for the magnets to obtain an appropriate field gradient is determined.

Figure 3:
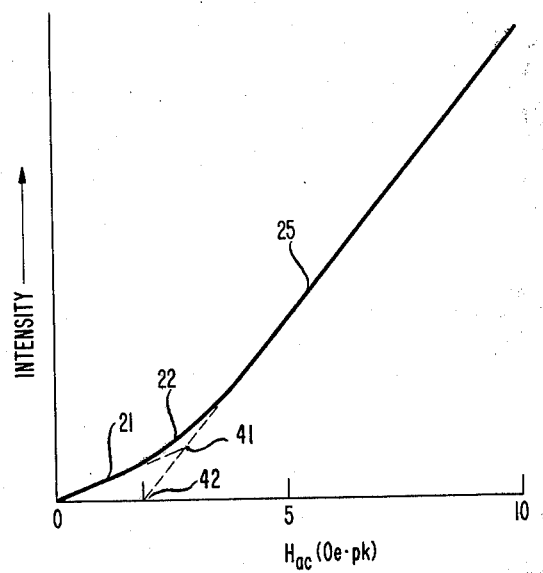
FIG. 3 is a graphic representation of the data obtained through the use of the subject invention.

To measure coercivity, a domain supporting material having a finger domain pattern is subjected to a static magnetic field with an appropriate spatial gradient as previously discussed. An AC field with a component perpendicular to the surface of the domain supporting material is then introduced by a conventional technique such as by using coils, 36, in FIG. 5. (It should be noted that it is sufficient if the static field and the AC field are components of the total field. It is possible to produce this total field by a single magnetic source or form a plurality of sources.) The perpendicular component of the AC field for practical application should have a maximum peak amplitude of not more than approximately 20 Oe, preferably not more than 10 Oe. Generally the frequency for this AC field is not critical and is in the range of 1 Hz to 10,000 Hz, preferably in the range of 100 to 1000 Hz. The AC field induces the movement of the ends of the finger domains. In a preferred embodiment, the peak amplitude of the AC field is varied between essentially zero and the desired maximum peak amplitude. A graph is made of the minority domain movement versus the peak amplitude of the AC field. The domain movement is advantageously monitored by using the Faraday effect discussed above. The light is monitored using a photomultiplier tube and the movement of finger domains produces a modulation of the total light intensity in the measurement area. A plot of the modulation amplitude of the light versus the varying amplitude of the perpendicular AC field component produces curves such as shown in FIG. 3 with a steep linear portion, 25. (For highly coercive materials there may not be a linear portion. In this case, the maximum peak AC field amplitude is increased to give the desired steep linear portion. This increase may make it necessary to exceed a maximum amplitude of 20 Oe although, as previously discussed, this is generally not desirable.)

An extrapolation of the steep portion of the curve thus obtained, i.e., extrapolation of section 25 in FIG. 3 yields a measure of the coercivity of the material. For most materials, the value obtained by the procedure is slightly higher than the actual value measured by the bubble translation technique. However, the proportionality between the measured and actual value is consistent for all measurements. In the preferred embodiment, to calibrate the measurement procedure, a sample with known coercivity is measured both by the bubble translation and by the subject process. A proportionality factor is then determined from this measurement and this proportionality factor is used to adjust subsequent measurements.

The proportionality is affected by the method of extrapolation. If extrapolation is done by determining the intersection, 41, of a tangent to the steep linear portion with a line tangent to the curve at the origin (21 in FIG. 3), a proportionality constant is obtained which is higher in value than that obtained by extrapolating the steep linear portion to zero domain movement, 42, e.g., zero light modulation amplitude. Irrespective of the particular extrapolation technique, the coercivity values attained are proportional to the value determined by the bubble translation method.

It should be noted that the subject measurement technique is particularly adaptable to manufacturing control. It is possible to accurately and expeditiously measure the coercivity of a sample from a group of domain supporting materials that were produced in a single batch. This value can then be used to insure that the materials have the desired coercivity and can be used to compare coercivities with materials from other batches.

We claim:

1. A method of measuring coercivity in materials capable of supporting single wall magnetic domains by observing a movement of domain patterns in said material, which movement is capable of being related to said coercivity, comprising the steps of producing a domain pattern in said material, subjecting said domain pattern to an AC magnetic field and monitoring in a region of said material the movement of said domain pattern induced by said AC magnetic field characterized in that at least 70 percent of the minority domains in said region satisfy the requirements that the minority domain (1) terminates at a point in said region, (2) is at least within 10 degrees of being parallel to the nearest neighbor minority domain, and (3) beyond an imaginary line passing through said point and perpendicular to the direction defined by a least-squares-fit-line of a boundary of said minority domain, has no other minority domain that both has a terminus within and extends beyond a separation distance of said point, where said separation distance is 10 $\mu$m; and where said domain pattern in said region is subjected to a static magnetic field having a mean spatial gradient less than 10 Oe/$\mu$m.

2. The method of claim 1 wherein said mean spatial gradient is less than 1 Ce/$\mu$m.

3. The method of claim 1 wherein said material capable of supporting single wall domains comprises a material with a garnet crystal structure.

4. The method of claim 3 wherein said mean spatial gradient is less than 1 Oe/$\mu$m.

5. The method of claim 1 wherein said static magnetic field is produced by permanent magnets.

6. The method of claim 5 wherein said permanent magnets are arranged in a symmetrical configuration relative to the surface of said material.

7. The method of claim 1 wherein said movement of said domain pattern is monitored by optical means.

8. The method of claim 1 including the step of selecting said material as representative from a group of domain supporting materials whose coercivity properties are to be measured.

9. The method of claim 1 where said separation distance is 20 $\mu$m.

10. The method of claim 1 where said separation distance is 100 $\mu$m.

* * * * *

UNITED STATES PATENT AND TRADEMARK OFFICE
CERTIFICATE OF CORRECTION

PATENT NO. : 4,342,962
DATED : August 3, 1982
INVENTOR(S) : George P. Vella-Coleiro and Raymond Wolfe It is certified that error appears in the above—identified patent and that said Letters Patent is hereby corrected as shown below:

In the Specification, column 1, line 31, "to", first occurrence, should read --of--; line 50, "27" should read --21--. Column 2, line 49, "See" should read --(See--. Column 6, line 47, "Ce/µm" should read --Oe/µm--.

Signed and Sealed this

Thirtieth Day of November 1982

[SEAL]

Attest:

GERALD J. MOSSINGHOFF

Attesting Officer          Commissioner of Patents and Trademarks